United States Patent [19]
McCullough et al.

[11] Patent Number: 5,667,989
[45] Date of Patent: Sep. 16, 1997

[54] FUNGAL CELL WALL PROTEIN CLY4

[75] Inventors: John E. McCullough, Whitehouse Station; Judith Baymiller, Plainsboro, both of N.J.

[73] Assignee: Bristol-Myers Squibb Company, Princeton, N.J.

[21] Appl. No.: 414,685

[22] Filed: Mar. 31, 1995

[51] Int. Cl.$^6$ .......................... C12P 21/02; C12N 15/63; C12N 1/21; C07H 21/04
[52] U.S. Cl. ................. 435/69.1; 435/320.1; 435/252.3; 435/254.21; 536/23.7
[58] Field of Search .................... 536/23.7; 435/69.1, 435/320.1, 252.3, 254.21

[56] References Cited

U.S. PATENT DOCUMENTS 5,194,600  3/1993  Bussey et al. ..................... 536/23.74

OTHER PUBLICATIONS

H. Uemura et al., Yeast, vol. 11, pp. 1093–1101, 1995.
S. D. Leidich et al., The Journal of Biological Chemistry, vol. 270, No. 22, pp. 13029–13035, 1995.
L. H. Hartwell, "Macromolecule Synthesis in Temperature-sensitive Mutants of Yeast", *J. of Bacteiology*, May (1976), pp. 1662–1670.
L. H. Hartwell et al., "Genetic Control of the Cell Division Cycle in Yeast", *Science*, vol. 183, Jan. (1974), pp. 46–51.
R. K. Mortimer et al., "Genetic Mapping in Saccharomyces IV. Mapping of Temperature–Sensitive Genes and Use of Disomic Strains in Localizing Genes", *Genetics*, May (1973), pp. 33–54.

*Primary Examiner*—Robert A. Wax
*Assistant Examiner*—Kawai Lau
*Attorney, Agent, or Firm*—Timothy J. Gaul

[57] ABSTRACT

CLY4 gene, protein, vectors, and host cells. The gene product pCly4 is involved in fungal cell wall biosynthesis, making it a useful target for anti-fungal agents.

11 Claims, 2 Drawing Sheets

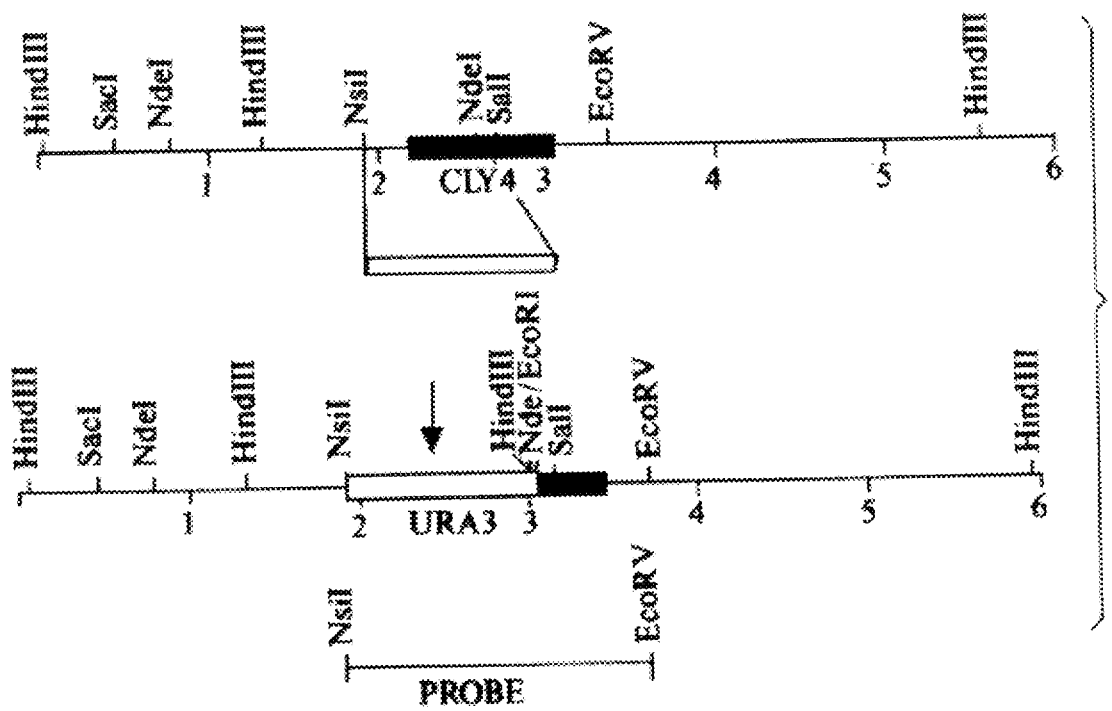
FIG. 3A
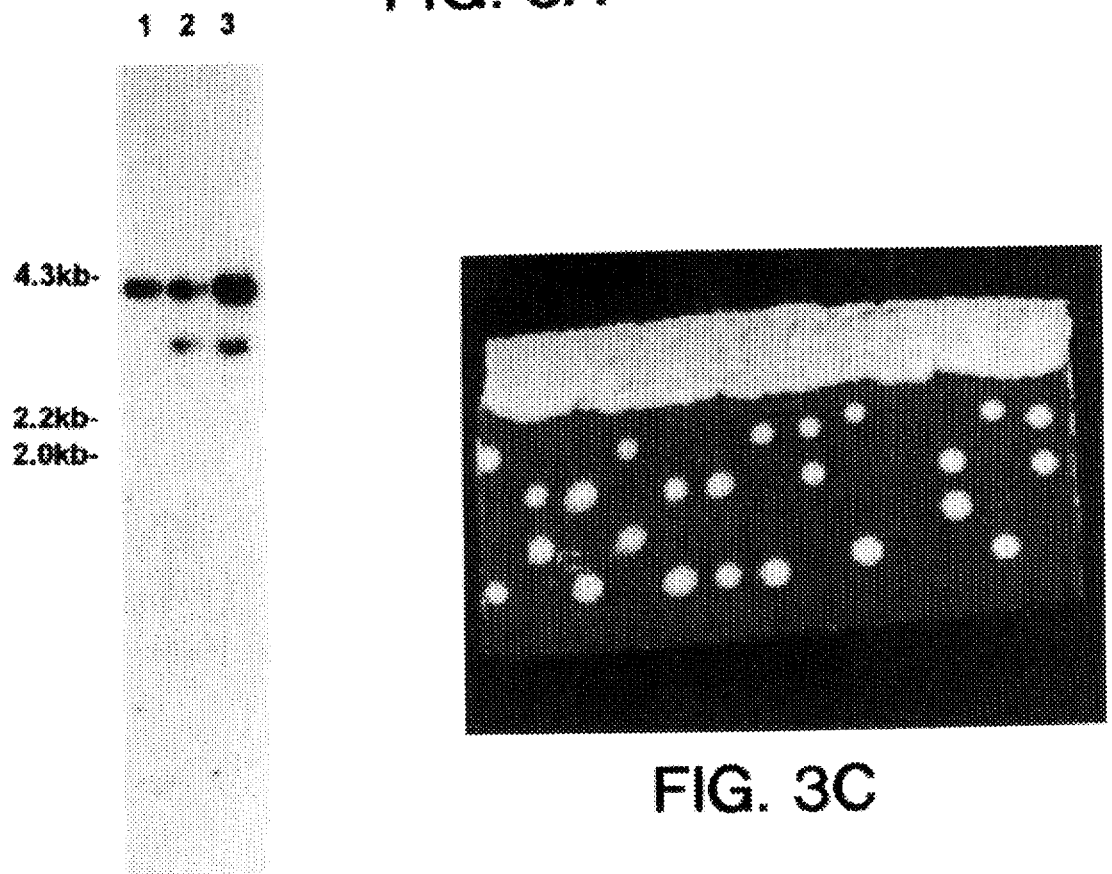
FIG. 3B
FIG. 3C 5,667,989

FUNGAL CELL WALL PROTEIN CLY4

FIELD OF THE INVENTION

The present invention relates to a gene, CLY4, associated with the cell wall of the yeast *Saccharomyces cerevisiae*, and more particularly to the identification, isolation and cloning of this gene. This invention also relates to use of this gene in screens for compounds with anti-fungal activity.

BACKGROUND OF THE INVENTION

The incidence of bacterial and fungal infections has increased dramatically over the last decade. One reason has been the increasing number of infections by human immunodeficiency virus (HIV), which causes AIDS.

AIDS is a vital infection targeting the CD4 lymphocytes of the immune system, leading to severe immunodeficiency. The World Health Organization estimates that at least 10 million people have been infected worldwide. J. M. Mann, *J. Infect. Dis.*, 165:245–250 (1992). In the United States, over 1 million are believed to be infected and over 250,000 have developed AIDS. S. M. Schnittman et al., *Advances in Internal Medicine*, 39:305–355 (1994). A rapid spread of AIDS is predicted for southeast Asia and India, home to more than one third of the world's population.

The morbidity and mortality associated with AIDS result primarily from subsequent infections, often with fungal pathogens. Fungal infections affect various organs and tissues, including lungs, mucous membranes, brain, and lymph nodes. These infections weaken patients, resulting frequently in hospitalization and sometimes in death. Fungal infections cause about 20% of AIDS-related deaths.

AIDS-related fungal infections mainly involve *Candida albicans*, *Cryptococcus neoformans*, *Aspergillus* and *Histoplasma*, with *Rhizopus*, *Mucor*, and *Blastococcus dermatitidis* less frequent. Candidosis, resulting from *C. albicans*, comprises about 80% of fungal infections in AIDS patients. Oropharyngeal candidosis, common among AIDS patients, is rarely fatal but is quite painful. Holmberg et al., *J. Infect. Dis.*, 18:179–184 (1986). Cryptococcosis, resulting from *Cryptococcus neoformans*, is less common but more likely to be lethal; it causes mortality of about 17% in its initial stages, 50 to 100% if relapse occurs. W. P. Powderly, *Textbook of AIDS Medicine* (S. Broder, T. C. Merigan Jr. & D. Bolgnesi, Eds.), William & Wilkins, Baltimore, Md. (1944), p. 345–357. Disseminated histoplasmosis is also quite lethal, with the chance of survival believed to be less than 60%.

In addition to AIDS patients, other populations are also immunocompromised and thus at great risk of infection. D. L. Brawner et al., *Clinical Microbiol.*, 27:1335–1341 (1989). Patients undergoing organ and bone marrow transplants are deliberately given immunosuppressants to prevent transplant rejection. Immunosuppression is incidental in other treatments, including cancer chemotherapy, oropharyngeal irradiation, antimicrobial chemotherapy, and corticosteroid treatment. Diabetes and indwelling catheters can also predispose patients to opportunistic infections. Another consideration is an aging population, since immune functions generally decline with age. G. B. Sefano et al., "Aging and Cellular Defense Mechanisms," *Ann. N.Y. Acad. Sci.*, 633:396 (1992).

Antibiotics have long been the first line of defense against infectious diseases. Many antibiotics with different modes of action are available, but few are antifungal. Moreover, the antifungal agents available are inadequate to treat many of the superficial and systemic mycoses that are prevalent.

The available antifungal agents comprise a small number of chemical types, such as polyene macrolides, synthetic azole compounds, griseofulvin, and 5-fluorocytosine. Especially active are polyene macrolides such as amphotericin B and nystatin. Introduced more than 30 years ago, amphotericin B is still the most potent antifungal drug for the treatment of deep-seated mycoses. Antifungal polyenes fight fungal pathogens by binding ergosterol, an essential sterol component of the fungal membrane. This binding allows formation of channels in the membrane and subsequent leakage of vital nutrients.

Polyenes may, however, cause severe side reactions. In addition to ergosterol, polyenes bind with lower affinity to cholesterol, a vital sterol in humans. As a result, polyenes may cause fever, disseminated intravascular coagulation, and even severe nephrotoxicity. Such nephrotoxicity may ultimately limit the dose administered, especially in conjunction with other nephrotoxic agents. J. Bratjburg et al., *Antimicrob. Agents Chemother.*, 34:183–188 (1990). Polyenes must then be administered parenterally at low doses over long periods, necessitating hospitalization and prolonged intravenous access. So in spite of the proven worth of amphotericin B, there is reluctance to use it.

In addition to polyenes, a number of azole antifungal agents have been introduced into clinical practice. This group includes imidazoles (ketoconazole and econazole) and the more recently introduced triazoles (fluconazole and itraconazole). Unlike polyenes, azoles effect antifungal activity by inhibiting a fungal P450 methylase involved in sterol biosynthesis.

Like polyenes, azoles may also cause a number of undesired side reactions. Ketoconazole and econazole also inhibit the biosynthesis of human phospholipids and sterols, as well as the activity of human P450 enzymes, mitochondrial cytochrome oxidase, and membrane-bound enzymes (e.g., plasma membrane ATPase). In addition, they are rapidly eliminated from the body, necessitating multiple dosing.

The triazoles inhibit their target fungal demethylase with greater specificity than the imidazoles. They have been widely used to treat superficial mycoses and, more recently, systemic mycoses. Since its introduction in 1988, fluconazole has been used to treat more than 15 million patients, including over 250,000 AIDS patients (A. A. Hitchcock, Biochemical Society Transactions). It has become the agent of choice for systemic candidosis (associated with cancer and organ transplants), oropharyngeal candidosis (associated with AIDS), and cryptococcal meningitis (also associated with AIDS).

Unfortunately, fluconazole and all other currently available azole antifungal agents have a number of flaws. First, they are fungistatic; i.e., they suppress the growth of but do not kill the pathogen. Such fungistatic activity is a major flaw in treatment of immunocompromised patients, who may suffer relapses. Second, resistance may be emerging. L. Willocks et al., *J. Antimicrob. Chemother.*, 28:937–9039 (1991). Although still relatively uncommon, resistant *C. albicans* strains have been reported after prolonged treatment with ketoconazole.

5-Fluorocytosine is a pyrimidine antifungal agent that is currently available. Originally developed as an antitumor agent, it acts by interfering with fungal DNA. After administration, it is transported into a susceptible fungal cell, deaminated to yield 5-fluorouracil, and subsequently converted to 5-fluorouridine triphosphate and 5-fluorodeoxyuridylate. The latter compound is a precursor of aberrant DNA, thus leading to aberrant protein. Although it has the advantage of oral availability, 5-fluorocytosine's usefulness is limited by the rapid emergence of resistance. In two studies cited by Kerridge et al., *Drugs of Today* 24:705–715 (1988), about 40% of strains examined were found to be partially resistant.

Griseofulvin is a natural product that affects the assembly of tubulin into microtubules (K. J. Weber et al., *J. Mol. Biol.*, 102:817–829 (1977). It is orally active, but its use is limited to topical dermatophytic infections.

Allylamines (naftifine and terbinafine) have been introduced for the treatment of dermatophytosis. These compounds inhibit squalene epoxidase, an enzyme involved in sterol biosynthesis. Like several other antifungal agents currently available, the allylamines have limited spectra and, therefore, limited usefulness.

In short, we face an increasing risk of fungal infection, armed with a number of drugs having various drawbacks. A need exists for new antifungal agents and methods for identification thereof.

To find and develop new anti-fungal agents, a new method of looking for them may be required. As noted by one researcher, "The major problem in obtaining clinically active anti-fungal chemotherapies stems from the fact that, in fungal infections, we are dealing with a eukaryotic pathogen in a eukaryotic host and from a structural point of view the two do not greatly differ from each other. Thus specific targets for attack by chemotherapy are not as evident as in the case of bacterial pathogens." R. A. Calderone et al., *Microbiol. Revs.*, 55:1–20 (1991).

One under-exploited target is the fungal cell wall. The cell wall is essential to growth of the yeast, because it contains many cell surface ligands and receptors that promote colonization of host cells and tissues. It is also essential to the protection of the yeast, because it provides rigidity to protect against osmotic injury. Since the fungal cell wall does not exist in man, it should provide differential screening targets—i.e., molecules identified should be more toxic to fungi than to man.

The synthesis of the cell wall in *S. cerevisiae* is mediated by a number of genes. The existence of temperature-sensitive mutations in *S. cerevisiae* causing cell lysis at non-permissive temperatures has been reported. L. H. Hartwell et al., *Science*, 183:46–51 (1974). The mutations were mapped to eight unlinked loci called CLY1-8. Hawthorne et al., *Genetics* 74:33–54 The lysis phenotype of these mutations suggests that these genes and their products can be utilized as differential targets in the search for antifungal agents.

*S. cerevisiae* has often been used as a surrogate for *C. albicans* in the development of screens for anti-fungal agents. D. R. Kirsch et al., *Current Opinion in Biotechnology*, 4:543–552 (1993). A vast amount of literature already exists about the physiology and genetics of *S. cerevisiae* and this organism is genetically more manipulable than is *C. albicans*, making it attractive as a test organism for study. Thus, genes involved in cell wall morphogenesis of *S. cerevisiae* may be used in screens for compounds that selectively inhibit yeasts and other fungi.

SUMMARY OF THE INVENTION

The present invention concerns an isolated nucleic acid molecule encoding the CLY4 protein. Preferably, the CLY4 protein is of *S. cerevisiae* origin and has the amino acid sequence of SEQ. ID. NO.: 2. Preferably, the nucleic acid molecule is a DNA (deoxyribonucleic acid) molecule, and the nucleic acid sequence is a DNA sequence. Further preferred is a nucleic acid having the nucleotide sequence shown in SEQ. ID. NO.: 1.

The present invention also concerns a nucleic acid molecule having a sequence complementary to the above sequences and 5', or 3' flanking regions thereof.

The present invention further concerns nucleic acid vectors comprising a DNA sequence coding for CLY4, host cells containing such vectors, and polypeptides comprising CLY4. Preferably, the polypeptide is full-length CLY4 or CLY4 recombinantly produced as described hereinafter.

The present invention also concerns methods for detecting nucleic acids coding for CLY4 and for detecting anti-fungal agents that target CLY4.

DESCRIPTION OF THE DRAWINGS

FIG. 3 shows the disruption of CLY4. (A) Strategy used to disrupt CLY4. Black box indicates the position of the CLY4 open reading frame, and the open box represents the URA3 gene. (B) Southern blot analysis of (1) W303, (2) and (3) independent of diploid disruptants. Chromosomal DNA was digested with HindIII and probed with the indicated probe. (C) Tetrad analysis of the disruption containing diploid (the strain whose DNA is in Lane 2 of southern.

DETAILED DESCRIPTION OF THE INVENTION

Definition of Terms

Figure 1:
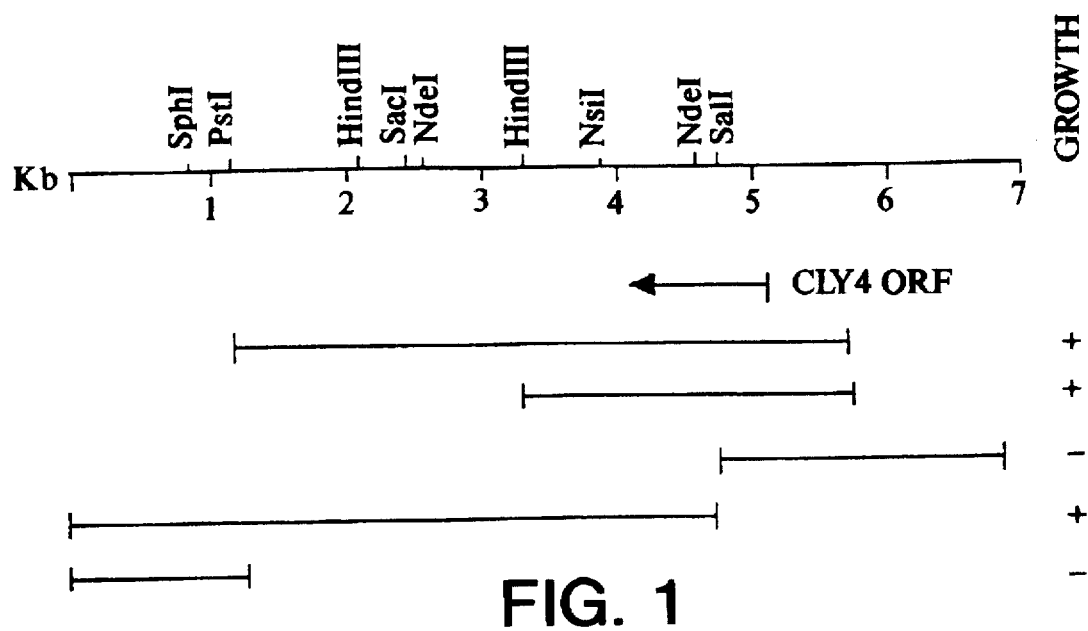
FIG. 1 shows the effect of deletions of pC407/pC408 insert on complementation of cly4-1 in SGY1324. The arrow indicates the direction and length of the CLY4 open reading frame. The lines at the bottom indicate the undeleted portion of the insert in each plasmid.

The following definitions apply to the terms as used throughout this specification, unless otherwise limited in specific instances:

"pCly4" refers to a polypeptide or protein complex that has the amino acid sequence of SEQ. ID. NO.: 2;

"allele" refers to one of two or more alternative forms of a gene;

"cloning" refers to isolation of a particular gene from the genome onto a plasmid or other vector;

"genome" or "genotyp" refers to the genetic constitution of an organism; i.e., a set of genes occurring in the organism;

"isogenic" refers to strains that have identical genomes that may have different plasmids;

"integrative" refers to a transformation of a yeast cell in which the transforming plasmid lacks an origin of replication, therefore requiring integration into the genome for propagation;

"multi-copy plasmid" refers to a plasmid having 10 to 30 copies present in a cell;

"nonpermissive" refers to a temperature at which a temperature-sensitive ("ts") mutant fails to grow;

"open reading frame" refers to a DNA sequence containing a series of nucleotide triplets coding for amino acids but lacking any termination codes;

"plasmid" refers to cytoplasmic, autonomously replicating chromosomal elements found in microorganisms;

"promoter" refers to a region on DNA at which RNA polymerase binds and initiates transcription;

"protrophy" refers to a strain's ability to grow without a particular nutrient such as an amino acid;

"Southern blot" refers to a method for identifying restriction fragments from a genomic restriction digest that contain a particular gene;

"stringent conditions" as used with respect to nucleic acid hybridization refers to Southern blotting washed in 0.1% SSC and 0.5% SDS at 58° C. Additional Southern blotting conditions are described in Maniatis et al., Molecular Cloning: A Laboratory Manual, Cold Spring Harbor Laboratory, Cold Spring Harbor, N.Y. (1982).

"tetrad analysis" refers to a method of analyzing the progeny of a yeast genetic cross by separating the four spores of the asci;

"transformant" refers to a yeast strain into which plasmid DNA has been introduced by transformation;

"URA3 gene" refers to the structural gene for orotidine-5' phosphate decarboxylase, which is required for uracil biosynthesis;

"wild type gene" refers to the form of a gene commonly found in nature; and

"control regions" refers to nucleotide sequences that regulate expression of a nucleic acid or any subunit thereof, including but not limited to any promoter, silencer, enhancer, splice site, transcriptional initiation element, transcriptional termination signal, polyadenylation signal, translational control element, translational start site, translational termination site, and message stability element. Such control regions may be located in sequences 5' or 3' to the coding region or in introns interrupting the coding region.

Additional definitions of common terms used in the course of this description of the invention may be found in F. Sherman et al., *Laboratory Course Manual for Methods in Yeast Genetics*, Cold Spring Harbor Laboratory, Cold Spring Harbor, N.Y. (1987).

Use and utility

The nucleic acids of the present invention can be used in a variety of ways in accordance with the present invention. For example, they can be used as DNA probes to screen other cDNA and genomic DNA libraries so as to select by hybridization other DNA sequences that code for proteins related to the CLY4 gene product, pCly4. In addition, the nucleic acids of the present invention coding pCly4 can be used as DNA probes to screen other cDNA and genomic DNA libraries to select by hybridization DNA sequences that code for CLY4 molecules from other organisms. The nucleic acids may also be used to generate primers to amplify cDNA or genomic DNA using polymerase chain reaction (PCR) techniques. The DNA sequences of the present invention can also be used to identify adjacent sequences in the cDNA or genome; for example, those that encode the gene, its flanking sequences and its regulatory elements.

The polypeptides and genes of the present invention are useful in assays for identification of antifungal agents. For example, they may be used in preparation of vectors, cells or cell lines used in such assays.

Various other methods of using the nucleic acids, polypeptides, expression vectors and host cells are described in detail below.

In carrying out the methods of the present invention, the agents that inhibit the expression or activity of pCly4 can be administered to various mammalian species, such as monkeys, dogs, cats, rats, humans, etc., in need of such treatment.

The agents that decrease the expression or activity of pCly4 can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), anti-oxidants (ascorbic acid or sodium bisulfite) or the like.

Process of preparation

In general

Cloning and sequencing of CLY4 provides the basis for the construction of plasmids that express high levels of pCly4. The plasmids, in turn, can be used to construct *S. cerevisiae* strains that can be used to screen for chemicals that inhibit the action of pCly4. Since pCly4 is required for cell viability, such inhibitors should inhibit cell growth. pCly4 can be overexpressed from its own promoter on a *S. cerevisiae* high copy number vector, or by placing it under the control of a strong yeast promoter. Overexpression should result in increased resistance to chemical agents that inhibit pCly4 action. A screen for pCly4 inhibitors entails comparing zones of growth inhibition of a strain overexpressing pCly4 and an isogenic strain not overexpressing pCly4.

Nucleic acids

The present invention concerns an isolated nucleic acid molecule comprising a nucleic acid sequence coding for pCly4. Preferably, the nucleic acid molecule is a DNA molecule and the nucleic acid sequence is a DNA sequence. Further preferred is a nucleic acid sequence having the nucleotide sequence shown in SEQ. ID. NO.: 1 or a nucleic acid sequence complementary thereto.

The cly4-1 allele was found in a screen for temperature-sensitive mutations in *S. cerevisiae* (L. H. Hartwell et al., Science, 183, 46–51, 1974). Preliminary analysis of its phenotype indicated that extensive cell lysis occurs when a strain containing the mutation is incubated at the nonpermissive temperature, indicating that CLY4 is required for cell wall integrity (L. H. Hartwell et al., Science, 183, 46–51, 1974). Lysis occurred in other *S. cerevisiae* strains containing this allele of CLY4 when incubated at the nonpermissive temperature.

Two plasmids with overlapping inserts were isolated that reproducibly complemented cly4-1. A *S. cerevisiae* strain was constructed having the selectable URA3 gene integrated at the chromosomal location of the common region of the inserts. This strain was crossed with a cly4-1 mutant. This cross demonstrated very tight linkage of CLY4 to the cloned insert, suggesting strongly that the insert contained the wild-type CLY4 gene.

DNA sequencing revealed that the insert also contained the yeast GCR1 and ATP4 genes flanking CLY4. No DNA sequence identical to that obtained for the region between GCR1 and ATP4 was listed in the GenBank database, showing that CLY4 was not previously isolated and hence is novel. Disruption of CLY4 showed that it is required for cell viability at all temperatures at which *S. cerevisiae* normally grows. CLY4 is located on chromosome XVI and is necessary for viability at 37° C.

With the *S. cerevisiae* CLY4 sequence in hand, other nucleic acids of the present invention can be obtained using various methods well-known to those of ordinary skill in the art. At least three alternative principal methods may be employed:

(1) the isolation of a double-stranded DNA sequence from genomic DNA or complementary DNA (cDNA) which contains the sequence;

(2) the chemical synthesis of the DNA sequence; and
(3) the synthesis of the DNA sequence by polymerase chain reaction (PCR).

In the first method, a genomic or cDNA library can be screened in order to identify a DNA sequence coding for pCly4. Various techniques can be used to screen genomic DNA or cDNA libraries for sequences encoding pCly4. This technique may, for example, employ a labeled single-stranded DNA probe with a sequence complementary to a sequence that encodes pCly4. For example, DNA/DNA hybridization procedures may be used to identify the sequence in the cloned copies of genomic DNA or cDNA which have been denatured to a single-stranded form. Suitable probes include cDNA for CLY4 acquired from the same or a related species, synthetic oligonucleotides, and the like.

A genomic DNA or cDNA library can also be screened for a genomic DNA or cDNA coding for pCly4 using immunoblotting techniques. In one typical screening method suitable for the hybridization techniques, a genomic DNA or cDNA library is first spread out on agarose plates, and then the clones are transferred to filter membranes (e.g., nitrocellulose). The genomic library is usually contained in a vector such as EMBL 3 or EMBL 4 or derivatives thereof (e.g., lambda DASH™). The cDNA library is usually contained in a vector such as λgt10, λgt11, or lambda ZAP. A DNA probe can then be hybridized to the clones to identify those clones containing the genomic DNA or cDNA coding for CLY4. Alternatively, appropriate *E. coli* strains containing vectors λgt11 or lambda ZAP can be induced to synthesize fusion proteins containing fragments of proteins corresponding to the cDNA insert in the vector. The fusion proteins may be transferred to filter membranes. An antibody may then be bound to the fusion protein to identify CLY4.

In the second method, nucleic acids coding for pCly4 can be chemically synthesized. The DNA sequence coding for pCly4 can be synthesized as a series of 50–100 base oligonucleotides that can then be sequentially ligated (via appropriate terminal restriction sites) so as to form the correct linear sequence of nucleotides.

In the third method, nucleic acids coding for pCly4 can be synthesized using PCR. Pairs of synthetic DNA oligonucleotides generally at least 15 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the PCR primers. See White, T. J. et al., *Trends Genet.* 5:185–9 (1989).

The nucleic acids coding for pCly4 can also be modified (i.e., mutated) to prepare various mutations. Such mutations may change the amino acid sequence encoded by the mutated codon, or they may be silent and not change the amino acid sequence. These modified nucleic acids may be prepared, for example, by mutating the nucleic acid coding for pCly4 so that the mutation results in the deletion, substitution, insertion, inversion or addition of one or more amino acids in the encoded polypeptide using various methods known in the art. Methods of site-directed mutagenesis am described in Taylor, J. W. et al., *Nucl. Acids Res.* 13, 8749–64 (1985) and Kunkel, J. A., *Proc. Natl. Acad. Sci. USA* 82, 482–92 (1985). In addition, kits for site-directed mutagenesis may be purchased from commercial vendors (e.g., Amersham Corp., Arlington Heights, Ill.). Disruption, deletion and truncation methods are described in Sayers, J. R. et al., *Nucl. Acids Res.* 16, 791–800 (1988).

Mutations may be advantageous in producing or using the polypeptides of the present invention. For example, these mutations may modify the function of the protein (e.g., result in higher or lower activity), permit higher levels of protein production or easier purification of the protein, or provide additional restriction endonuclease recognition sites in the nucleic acid. All such modified nucleic acids and polypeptide molecules are included within the scope of the present invention.

Expression vectors

The present invention further concerns expression vectors comprising a DNA sequence coding for pCly4. The expression vectors preferably contain the DNA sequence having the nucleotide sequence shown in SEQ. ID. NO.: 1. Further preferred are expression vectors comprising one or more regulatory DNA sequences operatively linked to the DNA sequence coding for pCly4. As used in this context, the term "operatively linked" means that the regulatory DNA sequences are capable of directing the replication and/or the expression of the DNA sequence coding for pCly4.

Expression vectors of utility in the present invention are often in the form of "plasmids", circular double stranded DNA loops that, in their vector form, are not bound to the chromosome. However, the invention is intended to include such other forms of expression vectors which serve equivalent functions and which become known in the art subsequently hereto. The expression vectors of the present invention may also be used to stably integrate the DNA sequence encoding pCly4 into the chromosome of an appropriate host cell (e.g., *E. coli, S. cerevisiae*).

Expression vectors useful in the present invention typically contain an origin of replication, a promoter located 5' to (i.e., upstream of) the DNA sequence, followed by the DNA sequence coding for pCly4, transcription termination sequences, and the remaining vector. The expression vectors may also include other DNA sequences known in the art, for example, stability leader sequences, which provide for stability of the expression product; secretory leader sequences, which provide for secretion of the expression product; sequences which allow expression of the structural gene to be modulated (e.g., by the presence or absence of nutrients or other inducers in the growth medium); marking sequences, which am capable of providing phenotypic selection in transformed host cells; restriction sites, which provide sites for cleavage by restriction endonucleases; and sequences which allow expression in various types of hosts, including prokaryotes, yeasts, fungi, plants and higher eukaryotes.

An expression vector as contemplated by the present invention is at least capable of directing the replication, and preferably the expression, of the nucleic acids of the present invention. Suitable origins of replication include, for example, the Col E1, the SV40 viral and the M13 orgins of replication. Suitable promoters include, for example, the cytomegalovirus promoter, the lacZ promoter, the gal10 promoter and the *Autographa californica* multiple nuclear polyhedrosis virus (AcMNPV) polyhedral promoter. Suitable termination sequences include, for example, the bovine growth hormone, SV40, lac Z and AcMNPV polyhedral polyadenylation signals. Examples of selectable markers include neomycin, ampicillin, and hygromycin resistance and the like. All of these materials are known in the art and are commercially available.

Suitable commercially available expression vectors into which the DNA sequences of the present invention may be inserted include the baculovirus expression vector pBlueBac, the prokaryotic expression vector pcDNAII and the yeast expression vector pYes2, all of which may be obtained from Invitrogen Corp., San Diego, Calif.

Suitable expression vectors containing the desired coding and control sequences may be constructed using standard recombinant DNA techniques known in the art, many of which are described in Sambrook et al., *Molecular Cloning: A Laboratory Manual*, Second Edition, Cold Spring Harbor Laboratory, Cold Spring Habor, N.Y. (1989).

Host cells

The present invention additionally concerns host cells containing an expression vector which comprises a DNA sequence coding for pCly4. See, for example the host cells of the working examples hereinbelow, which are preferred. The host cells preferably contain an expression vector which comprises all or part of the DNA sequence having the nucleotide sequence substantially as shown in SEQ. ID. NO.: 1. See, for example, the expression vector appearing in the examples hereinbelow, which is preferred. Further preferred are host cells containing an expression vector comprising one or more regulatory DNA sequences capable of directing the replication and/or the expression of and operatively linked to a DNA sequence coding for pCly4. Suitable host cells include both prokaryotic and eukaryotic cells. Suitable prokaryotic host cells include, for example, *E. coli* strains HB101, DH5a, XL1 Blue, Y1090 and JM101. Suitable eukaryotic host cells include, for example, Spodoptera frugiperda insect cells, COS-7 cells, human skin fibroblasts, and *S. cerevisiae* cells.

Expression vectors may be introduced into host cells by various methods known in the art. For example, transfection of host cells with expression vectors can be carried out by the calcium phosphate precipitation method. However, other methods for introducing expression vectors into host cells, for example, electroporation, liposomal fusion, nuclear injection, and viral or phage infection can also be employed.

Once an expression vector has been introduced into an appropriate host cell, the host cell may be cultured under conditions permitting expression of large amounts of the desired polypeptide, in this case a polypeptide molecule comprising CLY4.

Host cells containing an expression vector that contains a DNA sequence coding for pCly4 may be identified by one or more of the following six general approaches: (a) DNA-DNA hybridization; (b) the presence or absence of marker gene functions; (c) assessing the level of transcription as measured by the production of mRNA transcripts encoding pCly4 in the host cell; (d) detection of the gene product immunologically; (e) enzyme assay; and (f) PCR.

In the first approach, the presence of a DNA sequence coding for pCly4 can be detected by DNA-DNA or RNA-DNA hybridization using probes complementary to the DNA sequence.

In the second approach, the recombinant expression vector host system can be identified and selected based upon the presence or absence of certain marker gene functions (e.g., thymidine kinase activity, resistance to antibiotics, etc.). A marker gene can be placed in the same plasmid as the DNA sequence coding for pCly4 under the regulation of the same or a different promoter used to regulate the pCly4 coding sequence. Expression of the marker gene indicates expression of the DNA sequence coding for pCly4.

In the third approach, the production of mRNA transcripts encoding pCly4 can be assessed by hybridization assays. For example, polyadenylated RNA can be isolated and analyzed by Northern blotting or a nuclease protection assay using a probe complementary to the RNA sequence. Alternatively, the total RNA of the host cell may be extracted and assayed for hybridization to such probes.

In the fourth approach, the expression of CLY4 can be assessed immunologically, for example, by immunoblotting with antibody to pCly4 (Western blotting).

In the fifth approach, oligonucleotide primers homologous to sequences present in the expression system (i.e., expression vector sequences or CLY4 sequences) am used in a PCR to produce a DNA fragment of predicted length, indicating incorporation of the expression system in the host cell.

The DNA sequences of expression vectors, plasmids or DNA molecules of the present invention may be determined by various methods known in the art. For example, the dideoxy chain termination method as described in Sanger et al., *Proc. Natl. Acad. Sci. USA* 74:5463–7 (1977), or the Maxam-Gilbert method as described in *Proc. Natl. Acad. Sci. USA* 74:560–4 (1977) may be employed.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

Polypeptides

The present invention further concerns polypeptide molecules comprising pCly4, said polypeptide molecules preferably having the amino acid sequence shown in SEQ. ID. NO.: 2. All amino acid sequences are represented herein by formulas whose left to right orientation is in the conventional direction of amino-terminus to carboxy-terminus. The CLY4 *S. cerevisiae* DNA sequence shows that it encodes a 280 amino acid protein. The protein contains two long hydrophobic regions between residues 50 and 160 and between residues 175 and 250. The region in the middle between residues 160 and 175 and the ends of the protein are hydrophilic.

The polypeptides of the present invention may be obtained by synthetic means, i.e., chemical synthesis of the polypeptide from its component amino acids, by methods known to those of ordinary skill in the art. For example, the solid phase procedure described by Houghton et al., *Proc. Natl. Acad. Sci.* 82: 5131–5 (1985) may be employed. It is preferred that the polypeptides be obtained by production in prokaryotic or eukaryotic host cells expressing a DNA sequence coding for pCly4, or by in vitro translation of the mRNA encoded by a DNA sequence coding for pCly4. For example, the DNA sequence of SEQ. ID. NO.: 1 or any part thereof may be synthesized using PCR as described above and inserted into a suitable expression vector, which in turn may be used to transform a suitable host cell. The recombinant host cell may then be cultured to produce pCly4. Techniques for the production of polypeptides by these means are known in the art.

The polypeptides produced in this manner may then be isolated and purified to some degree using various protein purification techniques. For example, chromatographic procedures such as ion exchange chromatography, gel filtration chromatography and immunoaffinity chromatography may be employed.

The polypeptides of the present invention may be used in a wide variety of ways. For example, the polypeptides may be used to prepare in a known manner polyclonal or monoclonal antibodies capable of binding the polypeptides. These antibodies may in turn be used for the detection of the polypeptides of the present invention in a sample, for example, a cell sample, using immunoassay techniques, for example, radioimmunoassay, enzyme immunoassay, or immunocytochemistry. The antibodies may also be used in affinity chromatography for isolating or purifying the polypeptides of the present invention from various sources.

The polypeptides of the present invention have been defined by means of determined DNA and deduced amino acid sequencing. Due to the degeneracy of the genetic code, other DNA sequences which encode the same amino acid sequences depicted in SEQ. ID. NO.: 2 may be used for the production of the polypeptides of the present invention.

It should be further understood that allelic variations of the foregoing DNA and amino acid sequences naturally exist, or may be intentionally introduced using methods known in the art. These variations may be demonstrated by one or more amino acid changes in the overall sequence, such as deletions, substitutions, insertions, inversions or addition of one or more amino acids in said sequence. Such changes may be advantageous in producing or using the polypeptides of the present invention; for example in isolation of pCly4 or related polypeptides by affinity purification. Amino acid substitutions may be made, for example, on the basis of similarity in polarity, charge, solubility, hydrophobicity, hydrophilicity and/or the amphiphathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine; asparagine, glutamine; serine, threonine; phenylalanine, tyrosine. Other contemplated variations include salts and esters of the aforementioned polypeptides, as well as precursors of the aforementioned polypeptides, for example, precursors having N-terminal substituents such as methionine, N-formylmethionine and leader sequences. All such variations are included within the scope of the present invention.

Method for detection of nucleic acids

The present invention further concerns a method for detecting a nucleic acid sequence coding for pCly4 or a related nucleic acid sequence, comprising contacting the nucleic acid sequence with a detectable marker which binds specifically to at least a portion of the nucleic acid sequence, and detecting the marker so bound. The presence of bound marker indicates the presence of the nucleic acid sequence. Preferably, the nucleic acid sequence is a DNA sequence having all or part of the nucleotide sequence substantially as shown in SEQ. ID. NO.: 1, or is complementary thereto.

A DNA sample containing the DNA sequence can be isolated using various methods for DNA isolation which are well-known to those of ordinary skill in the art. For example, a genomic DNA sample may be isolated from tissue by rapidly freezing the tissue from which the DNA is to be isolated, crushing the tissue to produce readily digestible pieces, placing the crushed tissue in a solution of proteinase K and SDS, and incubating the resulting solution until most of the cellular protein is degraded. The genomic DNA is then deproteinized by successive phenol/chloroform/isoamyl alcohol extractions, recovered by ethanol precipitation, and dried and resuspended in buffer.

Also preferred is the method in which the nucleic acid sequence is an RNA sequence. Preferably, the RNA sequence is an mRNA sequence. Additionally preferred is the method in which the RNA sequence is located in the cells of a tissue sample. An RNA sample containing the RNA sequence may be isolated using various methods for RNA isolation which are well-known to those of ordinary skill in the art. For example, an RNA sample may be isolated from cultured cells by washing the cells free of medium and then lysing the cells by placing them in a 4M guanidinium solution. The viscosity of the resulting solution is reduced by drawing the lysate through a 20-gauge needle. The RNA is then pelleted through a cesium chloride step gradient, and the supernatant fluid from the gradient carefully removed to allow complete separation of the RNA, found in the pellet, from contaminating DNA and protein.

The detectable marker useful for detecting a nucleic acid sequence coding for pCly4 or a related nucleic acid sequence, may be a labeled DNA sequence, including a labeled cDNA sequence, having a nucleotide sequence complementary to at least a portion of the DNA sequence coding for pCly4.

The detectable marker may also be a labeled RNA having a sequence complementary to at least a portion of the DNA sequence coding for pCly4.

The detectable markers of the present invention may be labeled with commonly employed radioactive labels, such as $^{32}P$ and $^{35}S$, although other labels such as biotin or mercury may be employed. Various methods well-known to those of ordinary skill in the art may be used to label the detectable markers. For example, DNA sequences and RNA sequences may be labeled with 32P or 35S using the random primer method.

Once a suitable detectable marker has been obtained, various methods well-known to those of ordinary skill in the art may be employed for contacting the detectable marker with the sample of interest. For example, DNA-DNA, RNA-RNA and DNA-RNA hybridizations may be performed using standard procedures known in the art. In a typical DNA-DNA hybridization procedure for detecting DNA sequences coding for pCly4 in genomic DNA, the genomic DNA is first isolated using known methods, and then digested with one or more restriction enzymes. The resulting DNA fragments are separated on agarose gels, denatured in situ, and transferred to membrane filters. After prehybridization to reduce nonspecific hybridization, a radiolabeled nucleic acid probe is hybridized to the immobilized DNA fragments. The membrane is then washed to remove unbound or weakly bound probe, and is then autoradiographed to identify the DNA fragments that have hybridized with the probe.

The presence of bound detectable marker may be detected using various methods well-known to those of ordinary skill in the art. For example, if the detectable marker is radioactively labeled, autoradiography may be employed. Depending on the label employed, other detection methods such as spectrophotometry may also be used.

It should be understood that nucleic acid sequences related to nucleic acid sequences coding for pCly4 can also be detected using the methods described herein. For example, a DNA probe that has conserved regions of the S. cerevisiae CLY4 gene can be used to detect and isolate related DNA sequences (e.g., a DNA sequence coding for the pCly4 from C. albicans). All such methods are included within the scope of the present invention.

Methods for detecting CLY4 inhibitors

The present invention further concerns methods for detecting inhibitors of CLY4. A screen for pCly4 inhibitors entails comparing zones of growth inhibition of a strain overexpressing pCly4 and an isogenic strain not overexpressing pCly4.

Cloning and sequencing of CLY4 provides the basis for the construction of S. cerevisiae strains that can be used to screen for chemicals that inhibit the action of the CLY4 gene product (pCly4). Since pCly4 is required for cell viability, such inhibitiors should inhibit cell growth. pCly4 can be over-expressed from its own promoter on a *S. cerevisiae* multi-copy vector, or by placing it under the control of a strong yeast promoter. A. *S. cerevisiae* strain, SGY1139-pCH07 containing CLY4 expressed from its own promoter on a multi-copy vector pCH07 has been constructed. *S. cerevisiae* strains containing such plasmids will contain higher than normal concentrations of the CLY4 gene product. This should result in resistance to chemical agents that inhibit pCly4 action. A screen for pCly4 inhibitors would require a yeast strain such as SGY1139-pCH07 over-expressing pCly4 from a plasmid and an isogenic control strain containing the same plasmid lacking the CLY4 gene pYEP351. Both strains would be treated with test compounds, and those that inhibited the growth of the pCly4 over-expressing strain less strongly than the control strain would be potential pCly4 inhibitors.

Antisense molecules may be used to reduce the amount of pCly4. See Toulme and Helene, *Gene* 72: 51–8 (1988); Inouye, *Gene*, 72: 25–34 (1988); and Uhlmann and Peyman, *Chemical Reviews* 90: 543–584 (1990). CLY4 antisense molecules can be designed based on genomic DNA and cDNA, corresponding 5' and 3' flanking control regions, other flanking sequences, or intron sequences. Such antisense molecules include antisense oligodeoxyribonucleotides, oligoribonucleotides, oligonucleotide analogues, and the like, and may comprise about 15 to 25 bases or more. Such antisense molecules may bind noncovalently or covalently to the CLY4 DNA or RNA. Such binding could, for example, cleave or faciltate cleavage of CLY4 DNA or RNA, increase degradation of nuclear or cytoplasmic mRNA, or inhibit transcription, translation, binding of transactivating factors, or pre-mRNA splicing or processing. All of these effects would decrease expression of CLY4 and thus make the antisense molecules useful in a method of treatment for fungal infection.

Potential target sequences for an antisense approach include but are not limited to the DNA or RNA sequence encoding pCly4, its 5' and 3' flanking control regions, other flanking sequences, and nonclassic Watson and Crick base pairing sequences used in formation of triplex DNA.

Antisense molecules may also contain additional functionalities that increase their stability, activity, transport into and out of cells, and the like. Such additional functionalities may, for example, bind or facilitate binding to target molecules, or cleave or facilitate cleavage of target molecules.

Vectors may be constructed that direct the synthesis of antisense DNA or RNA. In this case, the length of the antisense molecule may be much longer.

Materials and Methods

DNA seouence analysis

The nucleotide sequence of the CLY4 gone was determined using the dideoxy termination method with the Sequenase kit (U S Biochemical Corp. Cleveland Ohio, U.S.A.) or on an Applied Biosystem (Foster City, Calif.) automated sequencer. Computer assisted searches and analyses of nucleic acid and protein sequences were performed with the GCG sequence analysis software package and the GenBank-EMBL data base (Univ. of Wisconsin, Madison, Wis.).

Yeast strains and media

Table 1 lists the source and relevant genotypes of the *S. cerevisiae* strains used in this study. The cly4-1 mutation was isolated by Hartwell et al., *Science*, 183, 46–51, 1974 from *S. cerevisiae* strain A364A. Cly4-1 containing strain 233 (a derivative of A364A) was obtained from the Yeast Genetic Stock Center (Univ. of California, Berkeley, Calif.). Strain 233 was crossed with W303-1A to obtain SGY1324, a leu2-112 cly4-1 containing strain, for transformation with the gene library and 1322-8a, ura3, cly4-1 strain. Diploid strain W303 was constructed by crossing W303-1A and W303-1B. Media employed were standard yeast media described by F. Sherman et al., *Laboratory Course Manual for Methods in Yeast Genetics*, Cold Spring Harbor Laboratory, Cold Spring Harbor, N.Y. (1987).

Yeast transformation and genetics

Yeast transformation was performed using spheroplasts according to the method of A. Hinnen et al., *Proc. Nat. Acad. Sci. USA*, 75: 1929–1933 (1978). Yeast genetic crosses and tetrad analyses were done using standard yeast methods. F. Sherman et al., *Laboratory Course Manual for Methods in yeast Genetics*, Cold Spring Harbor Laboratory, Cold Spring Harbor, N.Y. (1987).

Construction of SGY1139-PCH07

SGY1139-pCH07 was constructed by transformation of SGY1139 with pc407 using the method of A. Hinnen et al., *Proc. Natl. Acad. Sci. USA*, 75:1929–1933 (1978).

Gene disruption

Disruption of CLY4 was done by single-step gene disruption. T. L. Orr-Weaver et al., *Methods in Enzymol.*, 101:228–245 (1983). A HindIII-XbaI fragment of DNA containing the CLY4 gene was subcloned from pC409 (pYEP351 with the insert shown in FIG. 1 inserted at the BamHI site) into pBSIIKS (Stratagene, La Jolla, Calif.) to make pC409. See J. E. Hill et al., *Yeast*, 2: 163–167 (1986). DNA containing the *S. cerevisiae* URA3 gene was cut from pYEP24 with EcoRI and NsiI. The EcoRI end was blunt-ended using T4 DNA polymerase. This piece of DNA was inserted between the NdeI and NsiI sites of pC409 to make pC410. T4 DNA polymerase was used to blunt end the NdeI site. PC410 was cut with BglII and SnaBI and the 1.3 kb BglII-SnaBI fragment was used to transform diploid strain W303 selecting for Ura3.

DNA preparation and Southern blot

Yeast DNA was prepared from W303 and 2 independent Ura+ putative cly4::URA3CLY4 disruptants as described in F. Sherman et al., *Laboratory Course Manual for Methods in Yeast Genetics*, Cold Spring Harbor Laboratory, Cold Spring Harbor, N.Y. (1987). The DNA was digested with HindIII and electrophoresed on a 0.7% agarose (Sigma) gel. DNA was blotted to neutral nylon (Bios, San Diego, Calif.) and filters were hybridized and washed using standard procedures. J. E. Hill et al., *Yeast*, 2: 163–167 (1986). CLY4is on a 4.2 kb HindIII fragment in W303. Integration of the URA3 gene places a new HindIII site 1.5 kb from one end of this fragment. Therefore, when DNA from the diploids containing the disruption is cut with HindIII the cly4::URA3 containing fragment is cut into 2 pieces of 1.5 and 2.7 kb. The blot was probed with the EcoRV-NsiI DNA fragment containing the CLY4 open reading frame (FIG. 4). The probe only contains homology to the 2.7 kb HindIII fragment from the cly4::URA3 allele of the disrupted diploids.

The *S. cerevisiae* chromosome blot was obtained from Clonetech (Palo Alto, Calif. It was probed with the same probe used for the southern blot (FIG. 3).

Radiolabeled DNA was prepared by nick-translation using the BRL kit with [$^{32}$P]dCTP (Dupont, Wilmington, Del.). Autoradiography was performed for appropriate time at -70° C. using Kodak X-Omat AR film with a Lightning Plus screen (Dupont, Wilmington, Del.).

Integration of URA3 gene at pC407 chromosomal locus

URA3 was inserted at the pC407 chromosomal locus by integrative transformation. T. L. Orr-Weaver et al., *Methods in Enzymol.*, 101: 228–245 (1983). PC407 was cut with SacI and SalI and the 2.1 kb fragment containing the CLY4 gene was inserted into pRS306, which had previously been cut with the same two enzymes, to make pC419. See R. Sikorski et al., *Genetics*, 122: 19–27 (1989). This placed the CLY4 gene within the multi-cloning site of this plasmid, close to the URA3 gone. The vector pRS306 is a yeast integrating vector lacking a DNA synthesis initiation sequence. It must integrate into the genome of a transformant to be passed along to the progeny of that transformant. The vector pC419 was cut at a restriction site (NdeI) within the CLY4 open reading frame to target integration at the chromosomal locus of the insert. The restricted DNA was transformed into *S. cerevisiae* strain W303-1A (genotype: CLY4, ura3-52), and transformant were selected on media lacking uracil.

RESULTS

Isolation of plasmids having a gene complementing cly4-1

The CLY4 gene was cloned from a *S. cerevisiae* gene library by complementation of the ts phenotype of the cly4-1 allele in strain SGY1324. SGY1324 was transformed with a gene library in the yeast vector pYEP351 selecting for leucine prototrophy. Transformants containing plasmids with genes that complement the ts phenotype were selected at the non-permissive temperature, 37° C. Plasmid DNA was isolated and amplified in *E. coli*. The cly4-1 mutant was again transformed and the transformants tested for complementation by incubation at 37° C. on YEPD agar. Two plasmids, pC407 and pC408 having overlapping inserts, contain a gene that reproducibly complements the ts mutation. The minimum complementing region of the insert was determined by deleting portions of the DNA inserts of pC407 and pC408 (FIG. 1). Plasmids containing these deletions were transformed into the cly4-1 containing strain SGY1324. Complementation was tested by examining growth at 37° C. on YEPD agar plates. As shown in FIG. 1, growth at the restrictive temperature was observed only when the region between the SalI and NsiI restriction sites is present on the plasmid.

Sequence of the DCly4-5 and pcly4-11 inserts

Figure 2:
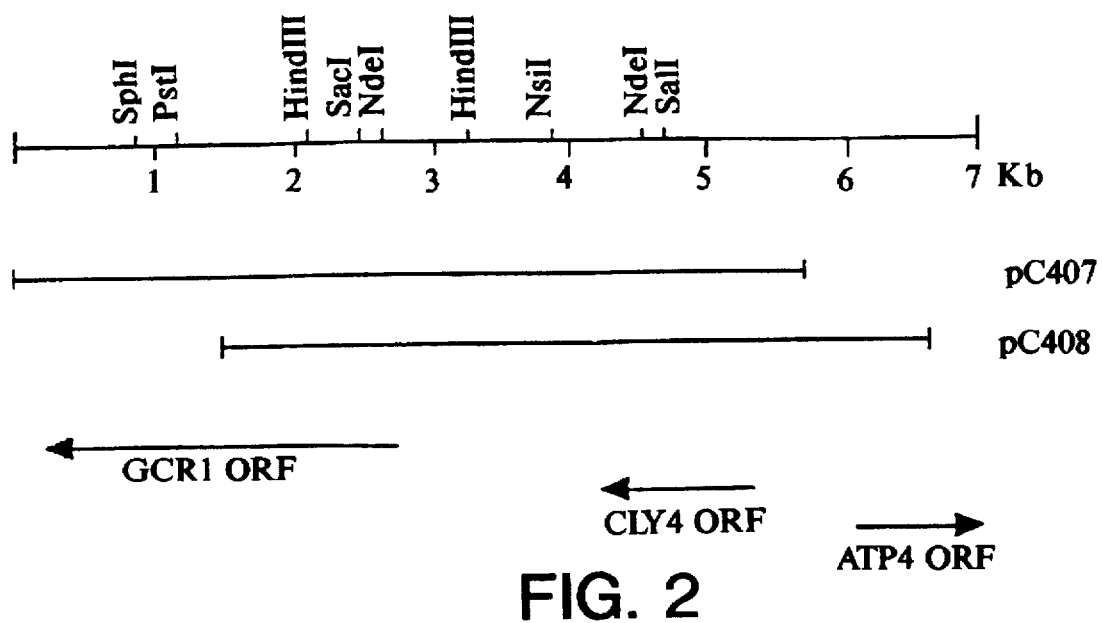
FIG. 2 shows a restriction map of the region of chromosome XVI containing the loci of GCR1, CLY4, and ATP4.

The pC407 and pC408 inserts were subcloned into pBSII for sequencing. Preliminary sequencing revealed that the previously identified yeast genes GCRI (M. J. Holland et al., *Mol. Cell. Biol.*, 7: 813–820 (1987)) and ATP4 (J. Velours et al., *Biochemie.*, 71: 903–915 (1989)) are present on the inserts of pC407 and pC408. These genes flank the complementing region of the insert (see FIG. 2 for orientation of GCRI, CLY4, and ATP4). The DNA sequence was determined as described above and is presented as SEQ ID NO: 1. There is one open reading frame in the complementing region encoding a protein of 280 amino acids (SEQ ID NO:2).

CLY4 is genetically linked to pcly4-5 and pcly4-11 inserts

To show that the sequenced insert contains the CLY4 gene and not some other gene that complements cly4-1 when expressed from a multi-copy plasmid, the URA3 gene was inserted into the genome of strain W303-1A as described above. This strain was crossed to the cly4-1 mutant strain 1322-8a (genotype cly4-1, ura3-52). If the plasmid insert contains the wild type CLY4 allele, then wild type CLY4 should be linked to URA3 in this cross and one would expect very few or no recombinant spores that have the Ura$^+$ ts$^-$ phenotype or the ura$^-$Ts$^+$ phenotype. There were no such recombinants from 29 tetrads dissected. Thus, the open reading frame is the CLY4 structural gene.

CLY4 is on chromosome XVI

A *S. cerevisiae* chromosome blot (Clonetech, Palo Alto, Calif.) was probed with a DNA fragment (EcoRV-NsiI, FIG. 4) containing the CLY4 coding sequence. The probe bound only to chromosome XVI.

Disruption of CLY4

To show that CLY4 is required for cell viability at all temperatures at which *S. cerevisiae* normally grows, disruption of CLY4 was done by single-step gene disruption. T. L. Orr-Weaver et al., *Methods in Enzymol.*, 101: 228–245 (1983). DNA containing the *S. cerevisiae* URA3 gene was cut from pYEP24 with EcoRI and NsiI and inserted within the CLY4 coding region between the NdeI and NsiI sites as shown in FIG. 3A. This results in the replacement of the coding sequence for the amino acids C-terminal of residue 141 with the coding sequence for URA3. This region of the enzyme is required for complementation of the cly4-1 allele. This construct was used to disrupt one of the CLY4 homologs of the diploid strain W303. Two strains containing the disruption were isolated and shown to have the disruption by southern blotting (FIG. 3B).

The existence of a ts allele of CLY4 indicates that the gene is required for cell viability. Therefore, a diploid strain was used for the disruption. The effect of the disruption on haploid cells was observed by sporulating the diploid containing the disruption, dissecting the spores, and observing the growth of the spores. For both of the disruption-containing diploids, only two of the four spores germinated and grew to visible colonies (FIG. 3C). All of the viable spores (from 30 tetrads) were Ura$^-$, clearly showing that the disruption is the cause of the loss of viability of the other spores.

Those spores receiving the cly4::URA3 disruption allele and, therefore, lacking a functional CLY4 gene grew normally for three generations and then stopped, presumably as the pCly4 originally present in the diploid was diluted. This result was observed at 20°, 25°, 30°, 34° and 37° C. Thus, CLY4 is required for cell viability at all temperatures between 20° and 37° C.

All references cited herein are hereby incorporated by reference. Strains with ATCC Accession Numbers are deposited in the American Type Culture Collection, 12301 Parklawn Drive, Rockville, Md. 20852-1776.

TABLE 1

| Strain | Genotype | Source |
|---|---|---|
| *Saccharomyces cerevisiae* | | |
| 233 | cly4-1 ade1 ade2 ura1 his7 lys2 tyr1 gal1 MATa | Yeast Genetic Stock Center |
| W303-1A | ade2 his3 leu2 trp1 ura3 MATa | Dr. Rodney Rothstein |
| W303-1B | ade2 his3 leu2 trp1 ura3 MATa | Dr. Rodney Rothstein |
| SGY1324 | ade1 leu2 ura1 | This study (ATCC Acc. No. 74333) |
| SGY 1322-8a | leu2 ura3 trp1 his3 | This study |
| SGY1139 (JN284) | ura3 leu2 | J. Nitiss |
| SGY 1139-CHO7 containing pCHO7 | ura3 leu2 | This study (ATCC Acc. No. 74334) |

What is claimed is:

1. An isolated nucleic acid molecule encoding the CLY4 protein comprising the amino acid sequence of SEQ. ID. NO.: 2.

2. The nucleic acid molecule of claim 1 comprising the nucleic acid sequence of bases 354 to 1193 of SEQ. ID. NO.: 1.

3. The nucleic acid molecule of claim 1 comprising the nucleic acid sequence of SEQ. ID. NO.: 1.

4. The nucleic acid molecule of claim 1 comprising a nucleic acid sequence that hybridizes to a molecule having a sequence complementary to SEQ. ID. NO.: 1 under stringent conditions.

5. A vector comprising the nucleic acid sequence of the nucleic acid molecule of claim 1.

6. A vector comprising the nucleic acid sequence of the nucleic acid molecule of claim 2.

7. A prokaryotic or eukaryotic host cell comprising the vector according to claim 5.

8. A prokaryotic or eukaryotic host cell comprising the vector according to claim 6.

9. The host cell of claim 7 that is ATCC 74334.

10. A method for producing a CLY4 protein, which comprises culturing a host cell according to claim 7 under conditions permitting expression of the protein.

11. A method for producing a CLY4 protein, which comprises culturing a host cell according to claim 8 under conditions permitting expression of the protein.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2074 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 354..1193

( x i ) SEQUENCE DESCRIPTION: SEQ ID NO:1:

```
TGAAGATAGT  GAATTGTAAA  TTTTTGGTTA  GGTTTTTCAA  AAACAATGTC  AATTACATGT      60

CAGCGAAGGC  CAGGTAGTAG  GTGTCCGTGG  CTATTGATTA  TCTTGATATC  CGAACTTGAG     120

ACCACTTCGC  GGCTACTAAA  TTTATGAACT  AAAAATGAAA  ATTTCAACTT  TGCATTACCT     180

CTTCGCTTTA  AACCAATTTA  AAGGTACAAT  CACACTTTAA  GTATTGTTGT  TAGACGGTGG     240

TGAATATAAT  CAGAGGCATC  CAAACTTTCT  GTTGCAGGTC  CATTATCCTC  TCAATTTTCG     300

TATGACCTTA  AAGAGACTTC  ATAGTTTATA  TTTGGTTATT  TTCAATAGGT  ACA ATG        356
                                                               Met
                                                                 1
```

```
ACA  AGA  TCT  CCC  TGG  AAG  CGC  CTA  CTA  TGG  TTG  AGA  CAG  GAA  TAC  CCA      404
Thr  Arg  Ser  Pro  Trp  Lys  Arg  Leu  Leu  Trp  Leu  Arg  Gln  Glu  Tyr  Pro
               5                        10                       15

GAT  AAT  TAT  ACA  GAT  CCA  AGT  TTT  ATT  GAG  TTG  AGA  GCA  AGA  CAA  AAG      452
Asp  Asn  Tyr  Thr  Asp  Pro  Ser  Phe  Ile  Glu  Leu  Arg  Ala  Arg  Gln  Lys
               20                       25                       30

GCT  GAG  AGT  AAC  CAG  AAG  TCT  GAT  AGA  AAA  TTA  TCA  GAA  GCT  GCT  CGC      500
Ala  Glu  Ser  Asn  Gln  Lys  Ser  Asp  Arg  Lys  Leu  Ser  Glu  Ala  Ala  Arg
     35                       40                       45

GCT  CAA  ATT  AGG  TTG  GAT  TTT  ATA  AGT  TTC  TAC  CAA  ACC  ATA  TTG  AAC      548
Ala  Gln  Ile  Arg  Leu  Asp  Phe  Ile  Ser  Phe  Tyr  Gln  Thr  Ile  Leu  Asn
50                       55                       60                       65

ACT  TCT  TTC  ATT  TAC  ATC  ACT  TTT  ACA  TAT  ATT  TAC  TAT  TAT  GGC  TTC      596
Thr  Ser  Phe  Ile  Tyr  Ile  Thr  Phe  Thr  Tyr  Ile  Tyr  Tyr  Tyr  Gly  Phe
                    70                       75                       80

GAT  CCT  ATT  CCG  CCA  ACT  ATT  TTC  CTT  TCA  TTT  ATT  ACA  TTG  ATT  ATA      644
Asp  Pro  Ile  Pro  Pro  Thr  Ile  Phe  Leu  Ser  Phe  Ile  Thr  Leu  Ile  Ile
               85                       90                       95

TCA  AGG  ACG  AAA  GTC  GAC  CCT  CTA  TTG  TCC  TCA  TTC  ATG  GAC  GTT  AAG      692
Ser  Arg  Thr  Lys  Val  Asp  Pro  Leu  Leu  Ser  Ser  Phe  Met  Asp  Val  Lys
          100                      105                      110

TCT  TCG  CTG  ATT  ATC  ACA  TTT  GCA  ATG  TTG  ACT  CTC  TCT  CCA  GTC  CTC      740
Ser  Ser  Leu  Ile  Ile  Thr  Phe  Ala  Met  Leu  Thr  Leu  Ser  Pro  Val  Leu
     115                      120                      125

AAA  TCT  CTT  TCT  AAG  ACA  ACT  GCA  TCT  GAT  TCC  ATA  TGG  ACA  TTG  TCT      788
Lys  Ser  Leu  Ser  Lys  Thr  Thr  Ala  Ser  Asp  Ser  Ile  Trp  Thr  Leu  Ser
130                      135                      140                      145

TTT  TGG  CTG  ACC  CTA  TGG  TAC  ATT  TTC  GTT  ATT  TCG  TCA  ACA  AAG  TCC      836
Phe  Trp  Leu  Thr  Leu  Trp  Tyr  Ile  Phe  Val  Ile  Ser  Ser  Thr  Lys  Ser
                    150                      155                      160

AAA  GAT  AAA  CCC  TCT  AAC  CTT  TCC  ACC  AAT  ATA  CTT  GTC  GCC  CTT  GTT      884
Lys  Asp  Lys  Pro  Ser  Asn  Leu  Ser  Thr  Asn  Ile  Leu  Val  Ala  Leu  Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 165 |     |     |     |     | 170 |     |     |     |     | 175 |     |      |
| GCT | GTC | CTA | TCA | TCG | AGG | CTT | TCG | ACC | ACA | ATC | GAC | GTA | TTC | TGT | TTT | 932  |
| Ala | Val | Leu | Ser | Ser | Arg | Leu | Ser | Thr | Thr | Ile | Asp | Val | Phe | Cys | Phe |      |
|     |     | 180 |     |     |     |     | 185 |     |     |     |     | 190 |     |     |     |      |
| CTT | TTG | ATT | TGT | ATT | CAG | TTG | AAT | ATC | ATT | CTA | CCC | ACT | TAT | TTA | TCG | 980  |
| Leu | Leu | Ile | Cys | Ile | Gln | Leu | Asn | Ile | Ile | Leu | Pro | Thr | Tyr | Leu | Ser |      |
|     | 195 |     |     |     |     | 200 |     |     |     |     | 205 |     |     |     |     |      |
| GTG | ACG | AAT | AAG | GTA | GTA | CCA | ATA | ATT | TCA | AAT | ATT | ATT | GTA | TAC | TCA | 1028 |
| Val | Thr | Asn | Lys | Val | Val | Pro | Ile | Ile | Ser | Asn | Ile | Ile | Val | Tyr | Ser |      |
| 210 |     |     |     |     | 215 |     |     |     |     | 220 |     |     |     |     | 225 |      |
| TTT | TTG | AAT | GTT | GCT | CTA | GGT | TGG | ATT | TAT | ATG | CTG | TTG | ATT | TTC | TTT | 1076 |
| Phe | Leu | Asn | Val | Ala | Leu | Gly | Trp | Ile | Tyr | Met | Leu | Leu | Ile | Phe | Phe |      |
|     |     |     |     | 230 |     |     |     |     | 235 |     |     |     |     | 240 |     |      |
| GCT | TCA | GTA | TTT | TAT | ATT | ACT | GTT | TTA | CCT | AAG | TGG | TTC | ATC | TAC | TGG | 1124 |
| Ala | Ser | Val | Phe | Tyr | Ile | Thr | Val | Leu | Pro | Lys | Trp | Phe | Ile | Tyr | Trp |      |
|     |     |     | 245 |     |     |     |     | 250 |     |     |     |     | 255 |     |     |      |
| AAA | ATC | AAT | TAT | CAT | AAA | CGG | GAT | AAC | GAT | CTA | CTA | AGT | ACA | TGG | GAT | 1172 |
| Lys | Ile | Asn | Tyr | His | Lys | Arg | Asp | Asn | Asp | Leu | Leu | Ser | Thr | Trp | Asp |      |
|     |     |     | 260 |     |     |     |     | 265 |     |     |     |     | 270 |     |     |      |
| GCA | AGA | ACA | CCA | ATA | TTG | GAT | TAGCGCAATC | AAGAACATGA | TTTCCTTCGG |     |     |     |     |     |     | 1223 |
| Ala | Arg | Thr | Pro | Ile | Leu | Asp |     |     |     |     |     |     |     |     |     |      |
|     | 275 |     |     |     |     | 280 |     |     |     |     |     |     |     |     |     |      |

| | | | | |
|---|---|---|---|---|
| ATAAGCAAGG | GAGGGGTACG | ACTTCTGCCC | GCAGGGGCTT | ATTGCTTGTC | CTCTTCCTCG | 1283 |
| ACCCCACGGT | ATTTCATTAT | ATATAGAGTC | ACTGTAATAA | TAATTATCAT | GAAACCTGAC | 1343 |
| AAGCAAAGGC | GTCGGGCAAT | TACCAAAGGG | CAGTTCGGTC | GATTAAGTTT | GCTTCACTAC | 1403 |
| AGATTATTCA | CATATCATAC | GACAACTTTA | AAATTGAACA | TTCAGGAGAT | TTTTGAATGC | 1463 |
| ATTGATGGGC | CCTTGCACCT | TAACCGAGTC | CCAATATTAG | AGAAACGCCC | CCTTAAACTG | 1523 |
| AACACAAGAC | AATACTACCT | GGCCAATAGC | GTACAATTTG | CGGCGTGTTA | AACAGGCGTT | 1583 |
| TCAGCGTCTA | CCGCTCCTAA | TTTAAAGTCA | CTTGTTTCTT | GGTAGCAGCA | GCTTCCTGTT | 1643 |
| TTCTTCTTTT | TGGCACTTGG | TTATGTGATA | ATATCACCCG | GATGAGAAAC | CTTTAAAATA | 1703 |
| AGCGTTTGGG | AGGGGAAAAA | GTGCAGTAAC | TGTCACAAAT | TTAACAAACA | ATTTGTTCAC | 1763 |
| AAGTTTTGCC | TTATCGTTCA | TCACATGTTA | TTTTTTTCAA | TCTAGCCAAA | GTATCTAAAG | 1823 |
| AAGAATTTTC | ATCTCTCTTG | TGCCTTCTCA | TAATGTTCAA | TTAAGATGCA | GACGGCTTTG | 1883 |
| ACATGTCATT | AATTTACTGA | ATTTCTGACA | CTTCCCCACG | ATATTTATCA | TTTTTTACGT | 1943 |
| AATTAAGATT | TAAACTCCGT | ACACCCGGCT | TCCACAAATG | TAGAATTTTC | CGGAGCTTCG | 2003 |
| AACTTCTTGT | TTCACGAATT | AAAAGCATCC | AACGTAGAAC | CACCCAACTC | ATCTTCCTAA | 2063 |
| TGCTGAAGCT | T | | | | | 2074 |

( 2 ) INFORMATION FOR SEQ ID NO:2:

( i ) SEQUENCE CHARACTERISTICS:
        ( A ) LENGTH: 280 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Thr | Arg | Ser | Pro | Trp | Lys | Arg | Leu | Leu | Trp | Leu | Arg | Gln | Glu | Tyr |
| 1 | | | | 5 | | | | | 10 | | | | | 15 | |
| Pro | Asp | Asn | Tyr | Thr | Asp | Pro | Ser | Phe | Ile | Glu | Leu | Arg | Ala | Arg | Gln |
| | | | 20 | | | | | 25 | | | | | 30 | | |
| Lys | Ala | Glu | Ser | Asn | Gln | Lys | Ser | Asp | Arg | Lys | Leu | Ser | Glu | Ala | Ala |
| | | | 35 | | | | | 40 | | | | | 45 | | |

```
Arg Ala Gln Ile Arg Leu Asp Phe Ile Ser Phe Tyr Gln Thr Ile Leu
    50              55                  60

Asn Thr Ser Phe Ile Tyr Ile Thr Phe Thr Tyr Ile Tyr Tyr Tyr Gly
65              70                  75                      80

Phe Asp Pro Ile Pro Pro Thr Ile Phe Leu Ser Phe Ile Thr Leu Ile
                85              90                      95

Ile Ser Arg Thr Lys Val Asp Pro Leu Leu Ser Ser Phe Met Asp Val
            100             105                     110

Lys Ser Ser Leu Ile Ile Thr Phe Ala Met Leu Thr Leu Ser Pro Val
        115             120                 125

Leu Lys Ser Leu Ser Lys Thr Thr Ala Ser Asp Ser Ile Trp Thr Leu
    130             135                 140

Ser Phe Trp Leu Thr Leu Trp Tyr Ile Phe Val Ile Ser Ser Thr Lys
145             150                 155                     160

Ser Lys Asp Lys Pro Ser Asn Leu Ser Thr Asn Ile Leu Val Ala Leu
                165             170                     175

Val Ala Val Leu Ser Ser Arg Leu Ser Thr Thr Ile Asp Val Phe Cys
            180             185                 190

Phe Leu Leu Ile Cys Ile Gln Leu Asn Ile Ile Leu Pro Thr Tyr Leu
        195             200                 205

Ser Val Thr Asn Lys Val Val Pro Ile Ile Ser Asn Ile Ile Val Tyr
    210             215                 220

Ser Phe Leu Asn Val Ala Leu Gly Trp Ile Tyr Met Leu Leu Ile Phe
225             230                 235                     240

Phe Ala Ser Val Phe Tyr Ile Thr Val Leu Pro Lys Trp Phe Ile Tyr
                245             250                 255

Trp Lys Ile Asn Tyr His Lys Arg Asp Asn Asp Leu Leu Ser Thr Trp
            260             265                 270

Asp Ala Arg Thr Pro Ile Leu Asp
        275             280
```